United States Patent
Niederberger

[11] Patent Number: 6,042,560
[45] Date of Patent: Mar. 28, 2000

[54] REGULATING DEVICE FOR A BREAST PUMP

[75] Inventor: Anton Niederberger, Oberdorf, Switzerland

[73] Assignee: Trimed AG, Triesen, Liechtenstein

[21] Appl. No.: 08/725,229

[22] Filed: Oct. 3, 1996

[30] Foreign Application Priority Data

Oct. 3, 1995 [CH] Switzerland .............................. 2773/95

[51] Int. Cl.$^7$ .................................................. A61M 1/06
[52] U.S. Cl. ................................................ 604/74; 604/73
[58] Field of Search .................................. 604/73, 74, 75, 604/76; 119/14.44; 251/42, 160, 345, 346, 352, 208

[56] References Cited

U.S. PATENT DOCUMENTS

| | | | |
|---|---|---|---|
| 1,751,591 | 3/1930 | McCloskey | 251/208 |
| 2,531,480 | 11/1950 | Sparklin et al. | 251/208 |
| 2,911,008 | 11/1959 | Du Bois | 251/208 |
| 3,323,774 | 6/1967 | Wilson | 251/352 |
| 3,782,385 | 1/1974 | Loyd | 604/74 |
| 4,673,388 | 6/1987 | Schlensog et al. | |
| 4,759,747 | 7/1988 | Aida et al. | 604/74 |
| 4,813,931 | 3/1989 | Hauze | 604/54 |
| 4,813,932 | 3/1989 | Hobbs | 604/74 |
| 4,883,464 | 11/1989 | Morifuki | 604/74 |
| 4,886,494 | 12/1989 | Morifuji | 604/74 |
| 4,946,134 | 8/1990 | Orlandi | 251/208 |
| 4,961,726 | 10/1990 | Richter | 604/74 |
| 4,964,851 | 10/1990 | Larsson . | |
| 5,007,899 | 4/1991 | Larsson . | |
| 5,071,403 | 12/1991 | Larsson . | |
| 5,308,040 | 5/1994 | Torres | 251/208 |

*Primary Examiner*—Gary Jackson
*Assistant Examiner*—Anthony S. King
*Attorney, Agent, or Firm*—Burns, Doane, Swecker & Mathis, L.L.P.

[57] ABSTRACT

The partial vacuum generated in a vacuum chamber by a suction pump via an air aspirating line and a hose can be changed by admitting leakage air through an air supply line. The supplied amount of leakage air is determined by a relative movement of a regulating groove and a leakage groove in respect to each other, and the partial vacuum in the vacuum chamber is regulated in this way. Since in a breast pump the partial vacuum generated in the vacuum chamber is transmitted to the funnel-shaped breast body, it is possible in this way to also regulate the partial aspiration vacuum over the breast.

7 Claims, 4 Drawing Sheets

REGULATING DEVICE FOR A BREAST PUMP

CROSS REFERENCE TO RELATED DOCUMENT

This application claims the benefit of the filing date of Switzerland Patent Application No. 2773/95, filed Nov. 18, 1996.

FIELD OF THE INVENTION

The invention relates to breast pumps for mother's milk, and more specifically to devices for regulating the partial vacuum in a vacuum chamber of a breast pump.

BACKGROUND OF THE INVENTION

Breast pumps are known and are used for aspirating and storing mother's milk, so that a baby can also be fed with natural mother's milk when its mother is absent. Such devices have a funnel-shaped breast body, which is connected via a suction body and a suction line with a manually or electrically operated suction pump.

A manually and motor-driven breast pump is described in U.S. Pat. No. 5,007,899, wherein the partial vacuum can be manually preselected in three stages by means of a switch disposed on the pump unit. Holes are provided for this in the pump cylinder, through which the amount of leakage air can be regulated, depending on whether one or two holes are opened for leakage air. In connection with this device it is disadvantageous that the partial vacuum cannot be set continuously adjustable and that the pump unit provided for this must have a large structure.

A battery-operated breast pump is described in U.S. Pat. No. 4,964,851, wherein the pump is placed directly on the aspirating unit. For regulating the partial vacuum a screw device is provided on the pump body which, by means of a rotary movement over several connected components, finally exerts a force on a spring which regulates the air intake. By means of this it is possible to obtain a continuous and continuously adjustable regulation of the partial vacuum. The complicated structure of this pressure regulation of this device is disadvantageous. In addition, handling has been shown to be unfavorable because of the accessibility of the screw device of the pressure regulator on the one hand, and on the other hand because it is necessary to move the pump unit together with the entire aspirating device.

Although breast pumps have been proven, they have the disadvantage that the partial vacuum generated in a vacuum chamber of the suction body, which is transmitted over the breast when the breast body has been applied, is solely determined by the output of the suction pump and cannot be changed at all or only in an unsatisfactory manner. Thus, with too low a partial vacuum the aspiration of the milk can be slow and inefficient, while it can be unpleasant and painful with too high a partial vacuum.

OBJECT AND SUMMARY OF THE INVENTION

It is therefore the object of the invention to prevent these disadvantages and to provide a device by means of which the partial vacuum in the vacuum chamber can be regulated.

This object is attained by means of a regulating device that is sealingly attached above the vacuum chamber and has an air aspirating line connecting it with the vacuum source as well as an air supply line connecting it via regulating elements with the atmosphere.

BRIEF DESCRIPTION OF THE DRAWINGS

A preferred embodiment of the invention is described with reference to the accompanying drawings, in which.

DETAILED DESCRIPTION OF THE PREFERRED EMBODIMENTS

Figure 1:
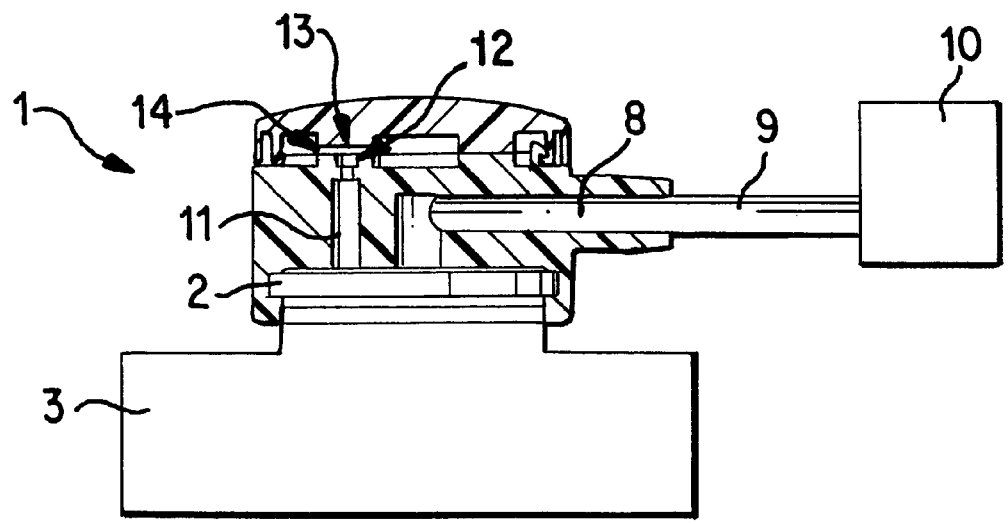
FIG. 1 is a sectional view of a regulating device placed on top of a vacuum chamber in accordance with this invention.
Figure 2:
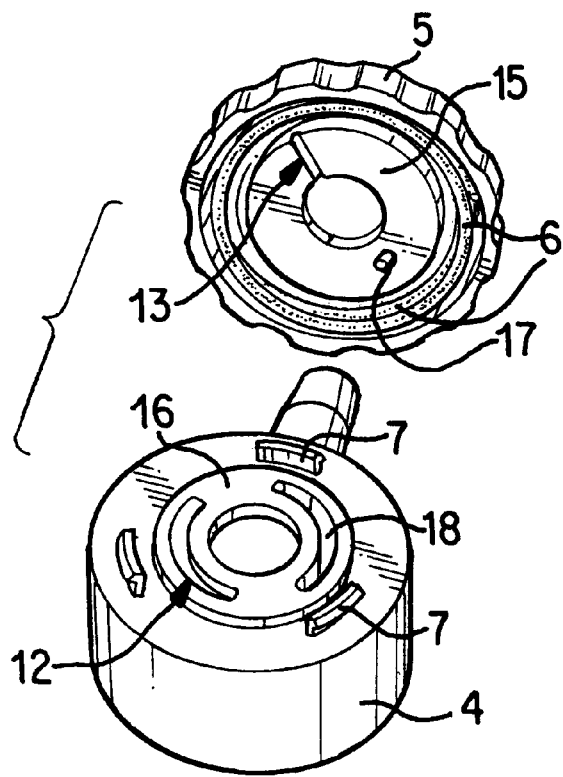
FIG. 2 is a diagrammatic representation of the regulating device of FIG. 1 with the cover removed.

In accordance with FIGS. 1 and 2, the regulating device 1 is sealingly attached over a bead 2 of the vacuum chamber 3, wherein preferably all parts are made of a thermoplastic material. Plastic materials which can be used are, for example, acrylonitrile-butadiene-styrol (ABS), polypropylene (PP), polyamides (PA), acetal resins (POM), polytetrafluoroethylene (PTFE), polyethylene (PE), polyvinylidene fluoride (PVDF), polyamides with approximately 20% PTFE, natural caoutchouc (with a Shore hardness D greater than 80). The regulating device 1 consists of a body 4 and a removable cover 5 having two circular beads 6, by means of which it can be rotatably seated on the body 4 while clamping three cams 7. An air aspirating line 8 in the body 4 connects the vacuum chamber 3 via a hose 9 with a suction pump 10. An air supply line 11 in the body 4 connects the vacuum chamber 3 with the atmosphere via a regulating groove 12 and a leakage groove 13 and adjoining labyrinth 14 in the cover 5. The leakage groove 13 has been cut into a circular cover regulating surface 15.

With the cover 5 installed, the cover regulating surface 15 of the cover 5 and a body regulating surface 16 provided on the body 4 are pressed together. In the process, the cams 7 provide the necessary tension during the clamping process. The cams 7 are designed in such a way that, after they have come into engagement with the beads 6, they can assure the pressure required for sealing the cover 5 in respect to the body 4. Starting at zero at one end of the regulating surface, the regulating groove 12 cut into the circular body regulating surface 16 widens evenly to its largest width at its other end. In this way by a constantly increasing area of the regulating groove, which may be generated either by width or alternatively by depth variation, the amount of the leakage air is controlled. A bolt 17 has been placed opposite the leakage groove 13 on the cover regulating surface 15 and engages a control or monitoring groove 18 of the body regulating surface 16 disposed symmetrically in respect to the regulating groove. It is possible in this way to displace the radially disposed leakage groove 13 over the entire length of the regulating groove 12 by rotating the cover. Since the dimensions of the leakage and the regulating grooves are correspondingly matched to each other, the appropriate amount of air can flow back into the vacuum chamber, so that at a suction output of the pump of, for example, 300 mm Hg, the partial vacuum in the vacuum chamber can be continuously set from 0 to 300 mm Hg in a continuously adjustable manner. The control groove 18 is advantageously embodied in such a way that in the course of the rotating movement of the cover 5 in respect to the body 4 it releases the leakage groove 13 until the leakage groove 13 comes to lie outside of the regulating groove 12, at which time a zero amount of leakage air has been reached. The bolt 17 can be embodied as an integral component of the cover 5. It can also be made of stainless steel or cut from a hard plastic material.

The ability to take the regulating device apart has a very considerable importance in respect to cleaning and maintenance. Because of this there is the possibility of cleaning all parts separately following use, by means of which the hygienic demands made on such a device are met.

Figure 3:
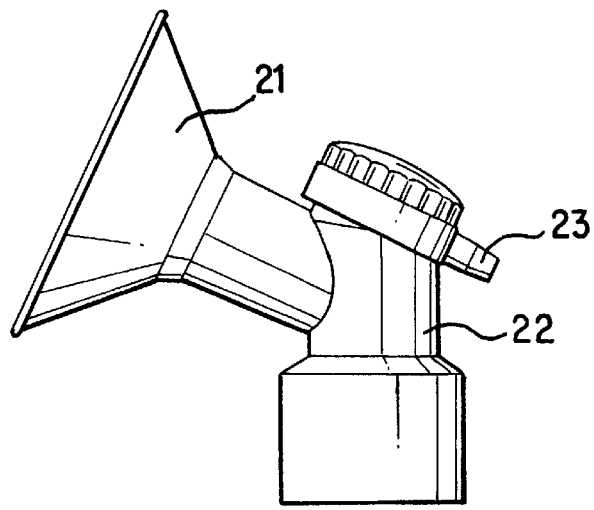
FIG. 3 is a side elevational view of a regulating device integrated into a breast pump.
Figure 4:
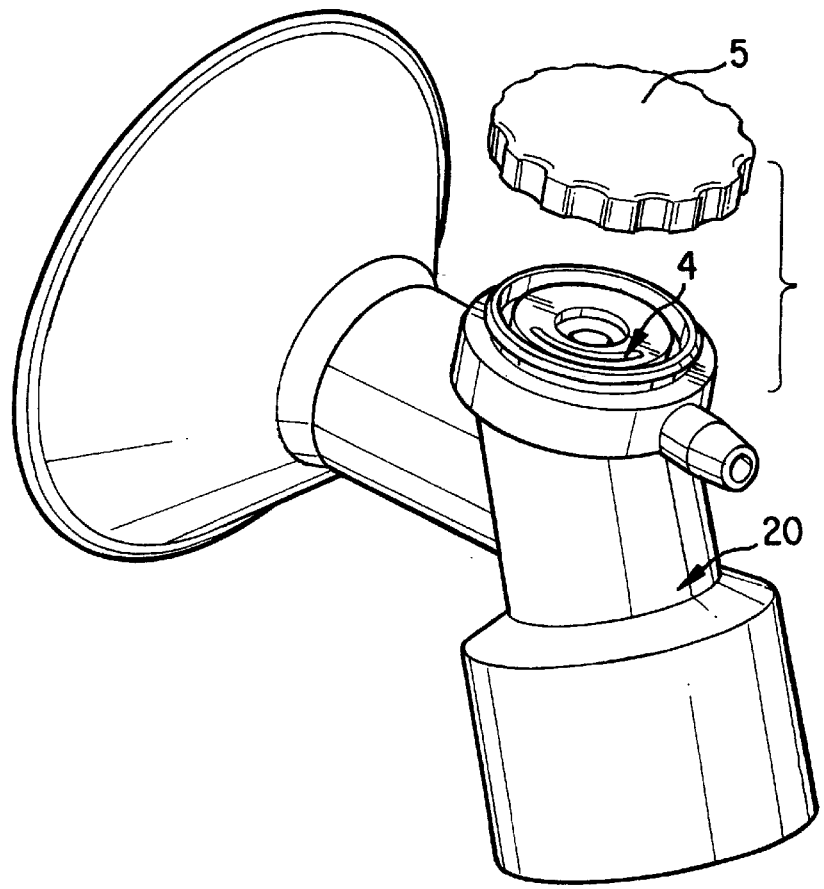
FIG. 4 is a top view of the breast pump of FIG. 3 with the cover removed from the regulating device.

The breast pump 20 represented in FIGS. 3 and 4 has a funnel-shaped breast body 21, which is connected with a suction body 22 containing the vacuum chamber, wherein the hose connecting the connecting sleeve 23 with the suction pump and the milk bottle, which can be screwed into the suction body, are not represented. The pump 20 is integrated on the body 4 of the regulating device and is injection-molded from plastic together with it in the same work step. The cover 5 can be clamped on the body 4 and by turning it, any desired partial vacuum can be set without delays and without time lags. The partial vacuum is generated by means of any known suction pump, which is operated manually or electrically by a battery, transformed low voltage or line voltage. This embodiment of a regulating device with an integrated pump has advantages in regard to production technology.

Figure 5:
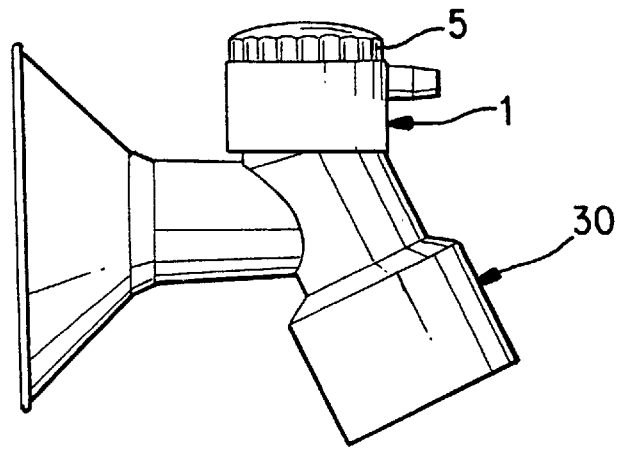
FIG. 5 is a side elevational view of a modified form of the breast pump with the regulating device placed on top of it.
Figure 6:
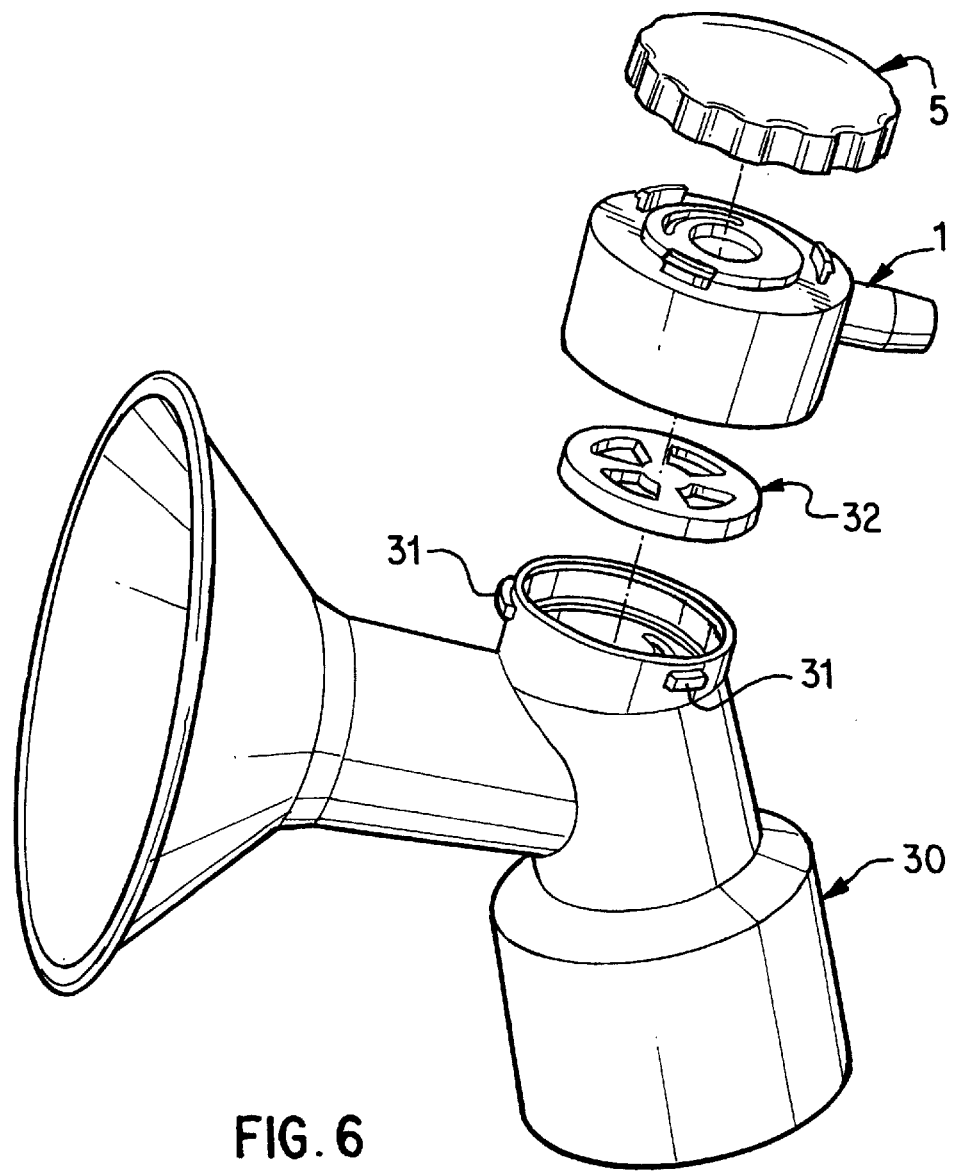
FIG. 6 is a top view of the breast pump in FIG. 5 with the regulating device parts lifted off.

In the breast pump 30 represented in FIGS. 5 and 6, the regulating device 1 with the cover 5 is placed on the pump by means of a bayonet catch 31. With this arrangement it is possible to install an overflow filter 32 and to exchange it when needed. Such an overflow filter prevents the contamination of the regulating device and, if required, also of the pump unit, which can be the case with large amounts of milk or during clumsy handling. Filter materials which are permeable to air and simultaneously impermeable to liquids are preferably employed. Such materials are generally known as microporous materials. A manually or motor-driven suction pump can be connected in this embodiment.

Figure 7:
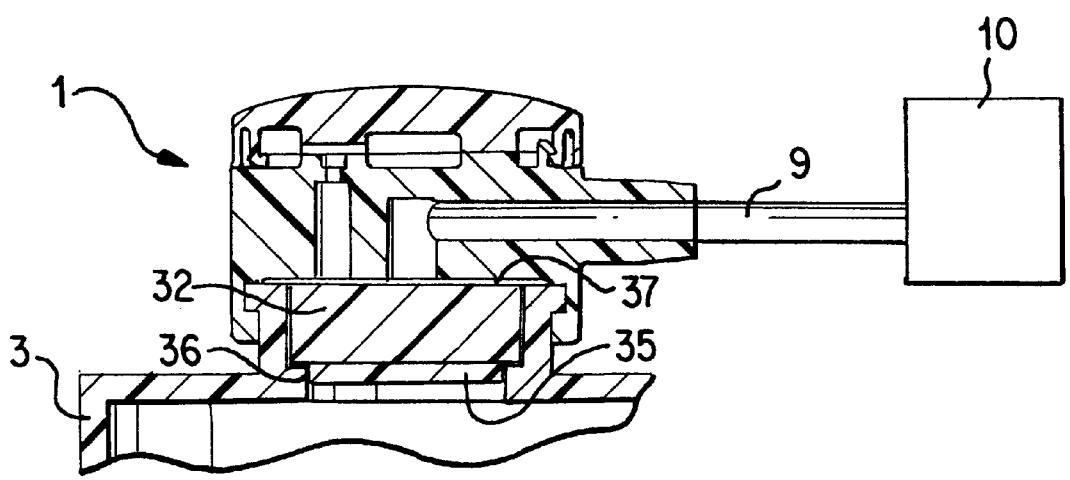
FIG. 7 is a sectional view of the regulating device in FIG. 6 with an overflow filter in the breast pump.

FIG. 7 shows a sectional view of a regulating device with an overflow filter and an aspirating device as described in FIG. 6. The overflow filter 32 has a cylindrical part 35 which here engages a collar 36 of the aspirating device. The overflow filter 32 is held in place and centered by this collar. On its top 37, the overflow filter 32 is delimited by the regulating device 1, which sealingly assures that no liquid can get into the regulating device from the aspirating device. The structure and function of the regulating device 1 has already been extensively described in FIGS. 1 and 2. For maintenance, the installation of such an overflow filter allows problem-free disassembly and afterwards simple cleaning or replacement. It is of course also possible to completely omit the insertion of an overflow filter in cases of small amounts of milk and with safe handling, which makes maintenance work minimal. It is therefore up to the user to select the most efficient way, on the one hand or, on the other hand, to choose the completely safe way of handling with an inserted overflow filter.

Viewed more generally, means are needed for preventing the contamination of the regulating device which make the entry of liquid media into the regulating device impossible. These means are not limited to overflow filters, but can also find use in the form of a check valve, for example.

Finally, it is also possible to combine two such regulating devices with attached breast pumps into a unit, so that the milk from two breasts can be simultaneously aspirated (double-pumping). The build-up of the partial vacuum can then take place alternatingly or simultaneously. However, an electrically operated suction pump is advantageously provided for such a unit, wherein the partial vacuum for each breast can be individually regulated, which is very much appreciated by the user.

Although the described regulating device is provided for a breast pump, it can be used for regulating a partial vacuum in any arbitrary device. In the process the amount of leakage air provided to the air supply line is regulated by a relative rotary movement of the regulating and the leakage grooves in respect to each other.

What is claimed is:

1. A regulating device comprising:
   (a) a vacuum source;
   (b) a vacuum chamber;
   (c) first passage means communicating between the vacuum source and the vacuum chamber;
   (d) second passage means communicating between the vacuum chamber and the atmosphere;
   (e) regulating means in the second passage means for leaking atmospheric air into the vacuum chamber to adjust the vacuum level in the vacuum chamber, the regulating means including a rotary cover having valve means for opening and closing the second passage means in response to rotation of the cover, a body, means for removably attaching the body to the vacuum chamber, and attachment means for attaching the cover to the body while permitting rotation of the cover relative to the body; and
   (f) preventing means in the first passage means for preventing fluid medium from entering the first passage, the preventing means including an overflow filter.

2. The regulating device according to claim 1 wherein the preventing means further includes a check valve.

3. A regulating device comprising:
   (a) a vacuum source;
   (b) a vacuum chamber;
   (c) first passage means communicating between the vacuum source and the vacuum chamber;
   (d) second passage means communicating between the vacuum chamber and the atmosphere;
   (e) regulating means in the second passage means for leaking atmospheric air into the vacuum chamber to adjust the vacuum level in the vacuum chamber, the regulating means including a rotary cover having valve means for opening and closing the second passage means in response to rotation of the cover, a body, means for removably attaching the body to the vacuum chamber, and attachment means for attaching the cover to the body while permitting rotation of the cover relative to the body; and
   (f) preventing means in the first passage means for preventing fluid medium from entering the first passage;
   wherein the regulating means includes a constantly variable size opening in the second passage.

4. A regulating device comprising:
   (a) a vacuum source;
   (b) a vacuum chamber;
   (c) first passage means communicating between the vacuum source and the vacuum chamber;
   (d) second passage means communicating between the vacuum chamber and the atmosphere;
   (e) regulating means in the second passage means for leaking atmospheric air into the vacuum chamber to adjust the vacuum level in the vacuum chamber, the regulating means including a rotary cover having valve means for opening and closing the second passage means in response to rotation of the cover, a body, means for removably attaching the body to the vacuum chamber, and attachment means for attaching the cover to the body while permitting rotation of the cover relative to the body; and (f) preventing means in the first passage means for preventing fluid medium from entering the first passage;

wherein the second passage means includes a curved regulating groove, a curved monitoring groove and a radially extending leakage groove.

5. The regulating device according to claim 4, wherein the regulating means includes a rotary cover, the body and the cover each having a regulating surface, the regulating groove and the monitoring groove being located on the regulating surface of the body in diametrically opposing relation to one another, and the leakage groove being located on the regulating surface of the cover.

6. A regulating device comprising:

(a) a vacuum source;

(b) a vacuum chamber;

(c) first passage means communicating between the vacuum source and the vacuum chamber;

(d) second passage means communicating between the vacuum chamber and the atmosphere;

(e) regulating means in the second passage means for leaking atmospheric air into the vacuum chamber to adjust the vacuum level in the vacuum chamber, the regulating means including a rotary cover having valve means for opening and closing the second passage means in response to rotation of the cover, a body, means for removably attaching the body to the vacuum chamber, and attachment means for attaching the cover to the body while permitting rotation of the cover relative to the body; and (f) preventing means in the first passage means for preventing fluid medium from entering the first passage;

wherein the rotary cover includes a regulating surface and a radial groove, the second passage means including a curved groove positioned to cooperate with the radial groove, the curved groove having a progressively larger area along the arc of the curved groove.

7. A regulating device comprising:

(a) a vacuum source;

(b) a vacuum chamber;

(c) first passage means communicating between the vacuum source and the vacuum chamber;

(d) second passage means communicating between the vacuum chamber and the atmosphere;

(e) regulating means in the second passage means for leaking atmospheric air into the vacuum chamber to adjust the vacuum level in the vacuum chamber, the regulating means including a rotary cover having valve means for opening and closing the second passage means in response to rotation of the cover, a body, means for removably attaching the body to the vacuum chamber, and attachment means for attaching the cover to the body while permitting rotation of the cover relative to the body; and (f) preventing means in the first passage means for preventing fluid medium from entering the first passage, the preventing means including a check valve.

* * * * *